(12) United States Patent
Thiele et al.

(10) Patent No.: US 6,814,951 B1
(45) Date of Patent: Nov. 9, 2004

(54) ACETALDEHYDE AND MALONDIALDEHYDE PROTEIN ADDUCTS AS MARKERS FOR ALCOHOL LIVER DISEASE

(75) Inventors: Geoffrey M. Thiele, Omaha, NE (US); Thomas L. McDonald, Omaha, NE (US); Dean J. Tuma, Omaha, NE (US); Lynell W. Klassen, Omaha, NE (US); Michael F. Sorrell, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/318,080

(22) Filed: May 25, 1999

Related U.S. Application Data

(62) Division of application No. 08/817,018, filed on Apr. 8, 1997, now Pat. No. 5,939,534.
(60) Provisional application No. 60/005,929, filed on Oct. 27, 1995.

(51) Int. Cl.[7] .................. A61K 49/00; A61B 10/00; G01N 33/564; C07D 211/70
(52) U.S. Cl. .................. 424/9.1; 424/9.6; 436/506; 546/315
(58) Field of Search .................. 424/9.1, 9.6, 278.1, 424/184.1; 436/506; 546/315, 1, 314; 530/402–406

(56) References Cited

PUBLICATIONS

Tuma et al. HEPATOLOGY, (Oct. 12, 1995) vol.22, No. 4, Part 2, Supp. S, pp. 479.*
Tani et al. "Enhancing Effect of Malondialdehyde Modification on the Mouse IgE Response to Protein Antigens", Argic. Biol. Chem, 1990, vol. 54:9 pp. 2323–2330.
Nair et al. "Novel Fluorescent 1,4–Dihydropyridines", Journ. Am. Chem. Soc., 1986, vol. 108:No. 26 pp 8283–8285.
Kikugawa et al. "Determination of Malondialdehyde in Oxidized Lipids by the Hantzsch Fluorometric Method", Analytic Biochemistry, 1988, vol. 174, pp. 512–521.
Beppu et al., "Interaction of Malondialdehyde–Modified Bovine Serum Albumin and Mouse Peritoneal Macrophages", Chem. Pharm. Bull., 1988, vol. 36, No. 11, pp. 4519–4526.
Ohya, Takeshi, "Formation of a New 1,1,1 Adduct in the Reaction of Malondialdehyde, n–Hexylamine and Alkanal under Neutral Conditions", Biol. Pharm. Bull., 1993, vol. 16(2) 137–141.
Bosron, et al., "Genetic Polymorphism of Enzymes of Alcohol Metabolism and Susceptibility to Alcoholic Liver Disease", Molec. Aspects Med., 1988, vol. 10, pp. 147–158.
Groopman, John D., et al., "Molecular Biomarkers for Human Chemical Carcinogen Exposures", Chem. Res. Toxicol., 1993, vol. 6, pp. 764–770.
Marco d'Ischia, et al., "Reaction of Malondialdehyde with Amine Neurotransmitters. Formation and Oxidation Chemistry of Fluorescent 1,4–Dihydropyridine Adducts", Tetrahedron, vol. 51, No. 34, pp. 9501–9508 (1995).
Tuma et al (Hepatology, 23:872–880) 1996.
Xu et al (Chemical Research in Toxicology, 10:978–986) 1997.
Kearley et al. (Chem. Res. Toxical., 12(1)100–105) 1999.

* cited by examiner

Primary Examiner—Gary B. Nickol
(74) Attorney, Agent, or Firm—McKee, Voorhees & Sease, P.L.C.

(57) ABSTRACT

A novel protein adduct is disclosed which is associated with the presence of alcohol liver disease. The adduct is a hybrid product of malondialdehyde and acetaldehyde which act synergistically to bind hepatic proteins. The adduct is highly immunogenic and fluorescent. Methods of detection are also disclosed including monoclonal and polyclonal antibodies.

3 Claims, 9 Drawing Sheets

ACETALDEHYDE AND MALONDIALDEHYDE PROTEIN ADDUCTS AS MARKERS FOR ALCOHOL LIVER DISEASE

RELATED U.S. APPLICATION DATA

This application is a divisional application of U.S. Ser. No. 08/817,018, filed Apr. 8, 1997 which was the National Stage of International Application No. PCT/US96/17833, filed Oct. 25, 1996 and further claims benefit to provisional application 60/005,929, filed Oct. 27, 1995, now abandoned.

GRANT REFERENCE

Work for this invention was funded in part by a grant from United States National Institute of Health Grant Nos. R01-04961-12 and 2R01-AA07818-04. The United States Government may have certain rights in this invention.

BACKGROUND OF THE INVENTION

The chronic consumption of alcoholic beverages is the major cause of serious liver disease. Ethanol is an extremely potent hepatoxin and can lead to cirrhosis of the liver upon prolonged exposure. In fact 20% of chronic alcoholics will eventually experience cirrhosis. The process of cirrhosis of the liver involves a series of steps beginning with fatty infiltration which leads to necrosis or cell death, then fibrosis which in turn leads to cirrhosis. Despite considerable research in this area, the underlying pathogenic mechanisms of ethanol induced liver injury, including the underlying biochemical reactions, remain obscure.

In recent years extensive evidence has come forward supporting a role of acetaldehyde in the detrimental actions of ethanol in liver as well as other organs. Numerous studies have shown that acetaldehyde can react with proteins in vitro under physiological conditions to form both stable and unstable adducts. Because of this chemical reactivity, the covalent binding of acetaldehyde to hepatic proteins has been proposed as a key event leading to alcohol liver injury. Many groups have demonstrated by immunoassays, using antibodies directed against acetaldehyde-modified protein, the presence of acetaldehyde adducts in the livers of rats, guinea pigs, and humans chronically consuming ethanol.

Studies involving the chemistry of acetaldehyde protein adduct formation have shown that acetaldehyde forms both unstable and stable adducts and that the $\epsilon$-amino group of lysine participates in binding and, further, that unstable adducts serve as intermediates in stable adduct formation. It has also been found that proteins contain lysine residues with varying reactivities towards acetaldehyde adduct formation and that certain proteins (such as $\alpha$-tubublin) may be selective targets for adduct formation by virtue of containing a specially reactive "key" lysine residue. Further information about acetaldehyde adducts is present in Tuma, D. J. "The Role of Acetaldehyde Adducts in Liver Injury", Hall P. Editors, Alcoholic Liver Disease Pathology and Pathogenesis, Ed. 2, London: Edward Arnold, 1995, 89–99 incorporated herein by reference.

The nature and/or chemical structures of acetaldehyde adducts that form in vivo have not been characterized and conflicting results in the literature concerning the nature, subcellular distribution, and identity of these adducts have been reported. See Tuma, D. J. "The Role of Acetaldehyde Adducts in Liver Injury", Hall P. Editors, Alcoholic Liver Disease Pathology and Pathogenesis, Ed. 2, London: Edward Arnold, 1995, 89–99 previously incorporated herein by reference.

Another reactive aldehyde involved in alcohol liver injury is malondialdehyde (MDA). Malondialdehyde is formed by the peroxidation of polyunsaturated fatty acids and from the oxidative degradation of deoxyribose by a hydroxy radical. MDA is also produced in mammalian tissues as a side product of prostaglandin and thromboxane biosynthesis.

Several studies have suggested that chronic ethanol consumption induces hepatic lipid peroxidation which in turn, generates malondialdehyde. MDA is toxic, mutagenic, and inactivates enzymes due to modification of lysine residues. MDA protein adducts have been detected in the liver following administration of agents that promote lipid peroxidation such as carbon tetrachloride, iron overload, and more recently chronic ethanol feeding. It has been shown to form an adduct with a lysine residue ($\epsilon$-amino group) of proteins and that MDA reacts with a primary amine to give a 1:1 Schiff base. For further information about MDA protein adducts see Houglum et al., J. Clin. Invest., 86: 1991 (1990) incorporated herein by reference.

Similar concentrations of acetaldehyde and MDA can co-exist in the liver during ethanol metabolism, as such both acetaldehyde and MDA adducts have been detected in livers of ethanol fed animals. Ohya demonstrates that malondialdehyde, in the presence of alkanals formed an adduct with the primary amine n-hexylamine. Ohya Parm. Bull. 16(2)137–141, February 1993. Due to the high levels of acetaldehyde and the production of malondialdehyde following alcohol ingestion applicants have discovered that the two aldehyde compounds chemically combine in a synergistic manner creating a new hybrid adduct formed with hepatic proteins. The hybrid adduct has been termed herein as malondialdehyde-acetaldehyde adduct (MAA). Although both aldehydes alone are capable of adduct formation with proteins, the influence of the presence of both acetaldehyde and MDA on adduct formation with complex proteins and their role in liver damage has not been addressed.

It is an object of the present invention to provide a novel protein adduct which occurs when malondialdehyde and acetaldehyde are combined and to delineate the role of both in adduct formation.

It is yet another object of the invention to provide a marker for alcohol liver damage which can be used to indicate the presence of liver disease, or other diseases with increased lipid peroxidation, lipids and/or or acetaldehyde which can include but is not limited to atherosclerosis or fat content for animals.

It is yet another object of the present invention to provide polyclonal and monoclonal antibodies which detect the presence of the novel acetaldehyde malondialdehyde protein adduct of the invention which can be used to assay for its presence.

It is yet another object of the present invention to define these novel acetaldehyde malondialdehyde protein adducts by chemical formulation.

It is yet another object of the invention to provide methods of use for the novel acetaldehyde malondialdehyde protein adduct in immunoassays such as FITC, FACS, and Western Blotting.

SUMMARY OF THE INVENTION

This invention discloses a novel reactant product of acetaldehydeand malondialdehyde (MDA) which interact together forming a novel compound which is highly reactive and is also adducted to antigens including complex proteins, lipids, carbohydrates or DNA simply by incubation of the two aldehydes with the antigen. The combination of MDA and acetaldehyde in the presence of various antigens causes a formation of a new distinct product comprising a hybrid adduct of MDA and acetaldehyde which has been designated malondialdehyde, acetaldehyde-adduct (MAA). These hybrid adducts are novel and the general chemical formula has been characterized. This is in stark contrast to most adducts which have not been so delineated, and provides opportunities for independent synthesis of the adduct itself and for creation of new antigen adduct combinations, as well as alternative assay methods.

According to the invention, the combination of MDA and AA in the presence of a protein or peptide creates two hybrid adducts which have been characterized at the molecular level having the following formulas. The hybrid adducts of the invention can include alterations at various functional groups which would not be expected to change the overall reactivity of the product. The formula for these hybrid adducts is listed below.

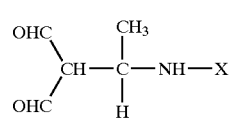

I.

Wherein X is an antigen which contains a reactive amino residue, and can be a peptide, protein, DNA molecule, carbohydrate or lipid. Compound I is associated with the presence of ALD and may be a better marker than compound II (MAA) except that it is less stable.

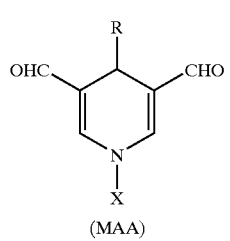

II.

(MAA)

Wherein R is a lower alkyl from C1 to about C6, H, or benzyl group and X is an antigen which contains a reactive amino residue, and can be a peptide, protein, DNA molecule, carbohydrate or lipid. These hybrid adducts are formed under standard conditions, by simple incubation.

In addition to the above-identified novel hybrid adducts, the adducts of the invention have several important immunological properties which can be exploited for further chemical and immunological assay procedures. Monoclonal and polyclonal antibodies have been produced which recognize these adducts and can be used to identify them as markers of alcohol liver disease or other diseases associated with increased lipid peroxidation, lipids, and/or acetaldehyde such as atherosclerosis and fat content for domestic animals.

MAA is highly reactive and will bind antigens preferentially to either acetaldehyde or malondialdehyde alone. Thus, MAA is a more sensitive indicator of the presence of concomitant liver disease. MAA also causes adducted proteins to become highly immunogenic. When used as an antigen, it produces high antibody titre and acts as a specific immune enhancing agent obviating the need for adjuvant. Without wishing to be bound by any theory it is postulated that MAA aids in antigen presentation of adducted proteins stimulating an immune response.

The MAA reaction product is highly fluorescent and the fluorescence is observed only when both aldehydes are co-incubated with the proteins. The fluorescence is large, has an excitation frequency of 398 nanometers and an absorbance of 460 nanometers. The fluorescence can be used as a label, allowing for detection of fluorescence at a picomolar range, enabling direct detection of antigen antibody complexes.

DESCRIPTION OF THE FIGURES

FIG. 3(a) depicts the relative fluorescence over an 8 hour time course with acetaldehyde (1.0 mM) and BSA (1 mg/ml) at 37° C. at various concentrations of MDA (0 to 8.0 mM). Results are mean+SE for five experiments.

FIG. 4(a) demonstrates specificity of the antibody. BSA was reacted for 3 days with acetaldehyde alone (1 mM) (circle); MDA alone (1 mM)(square); acetaldehyde (1 mM) and MDA (1 mM)(triangle) and native (untreated) BSA (inverted triangle).

FIG. 4(b) represents direct ELISA of the polyclonal antibody the affinity in the presence of 0.1 mM concentration of the aldehydes separately and together. As can be seen, the results are that of a typical ELISA demonstrating specificity of the affinity purified antibody to MAA adducts.

5(a) is a plot of percent inhibition of MAA adducts in terms of protein concentration.

5(b) depicts the data from 5(a) plotted as a function of bound acetaldehyde, indicating that the competitive ELISA adequately estimated the level of MAA modification of proteins and that the number of MAA epitopes is the most important determining factor in causing inhibition of antibody binding.

Figure 6A:
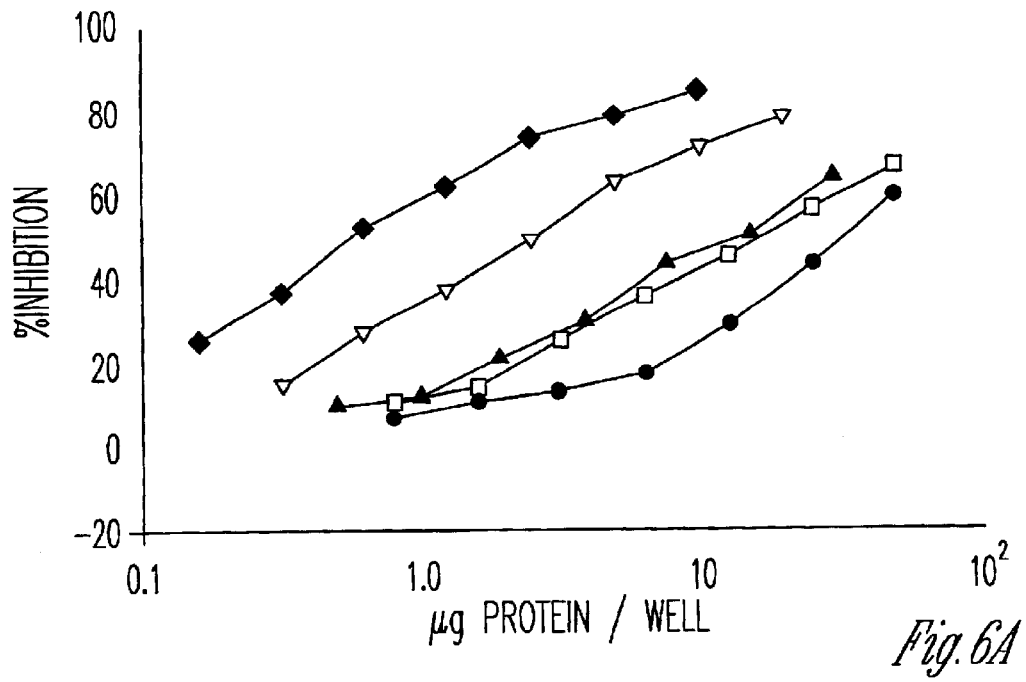
Figure 6B:
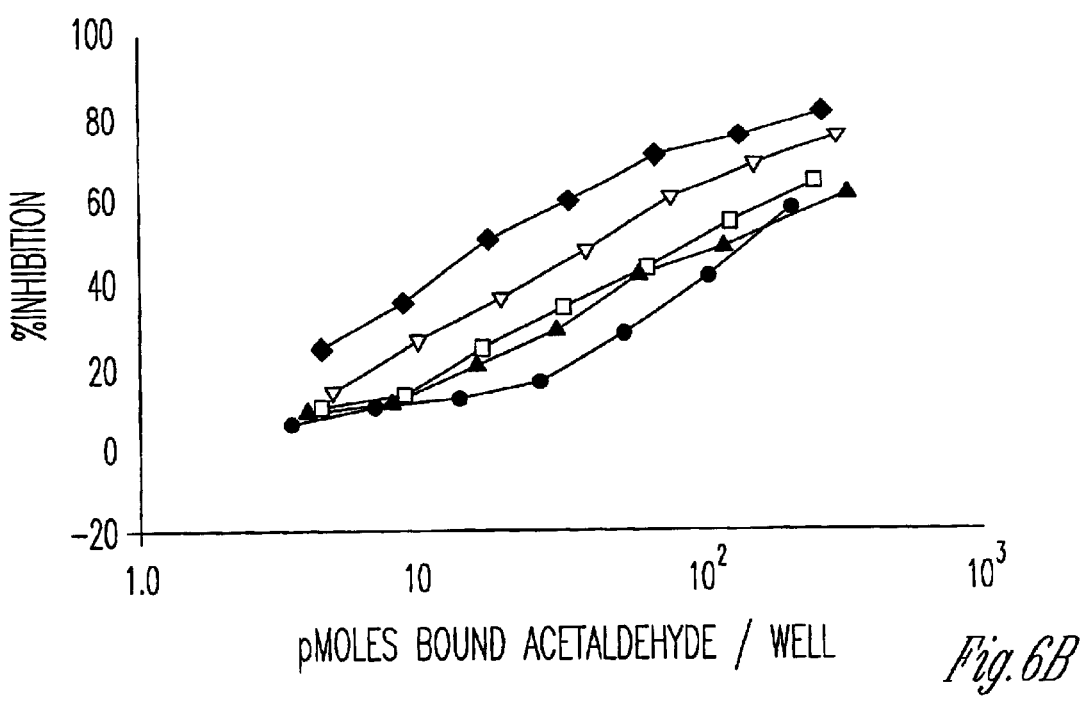

FIG. 6 represents competitive inhibition of cytosolic protein-MAA adducts in a competitive ELISA. Liver cytosolic proteins were derivatized with varying concentrations of MDA and acetaldehyde and bound acetaldehyde was quantified. Degree of modification based on mmoles of acetaldehyde bound per mg liver cytosol proteins was 28.2 (diamond); 16.0 (inverted triangle); 8.1 (triangle); 6.2 (square); and 4.3 (circle). FIG. 6(a) is percent inhibition in terms of protein concentration bound acetaldehyde.

Figure 7A:
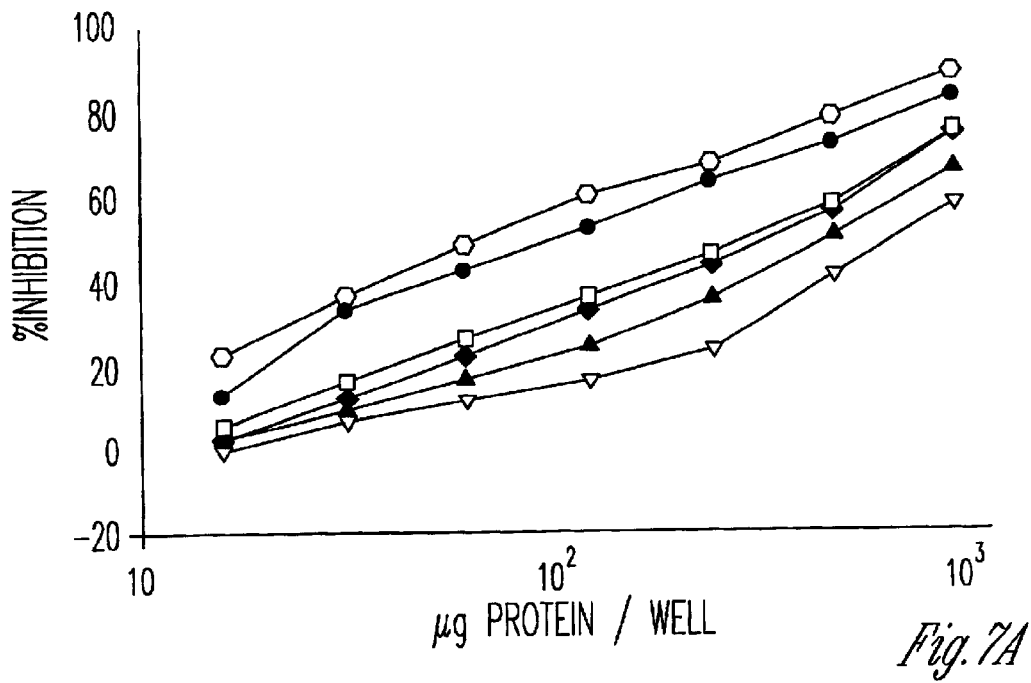
Figure 7B:
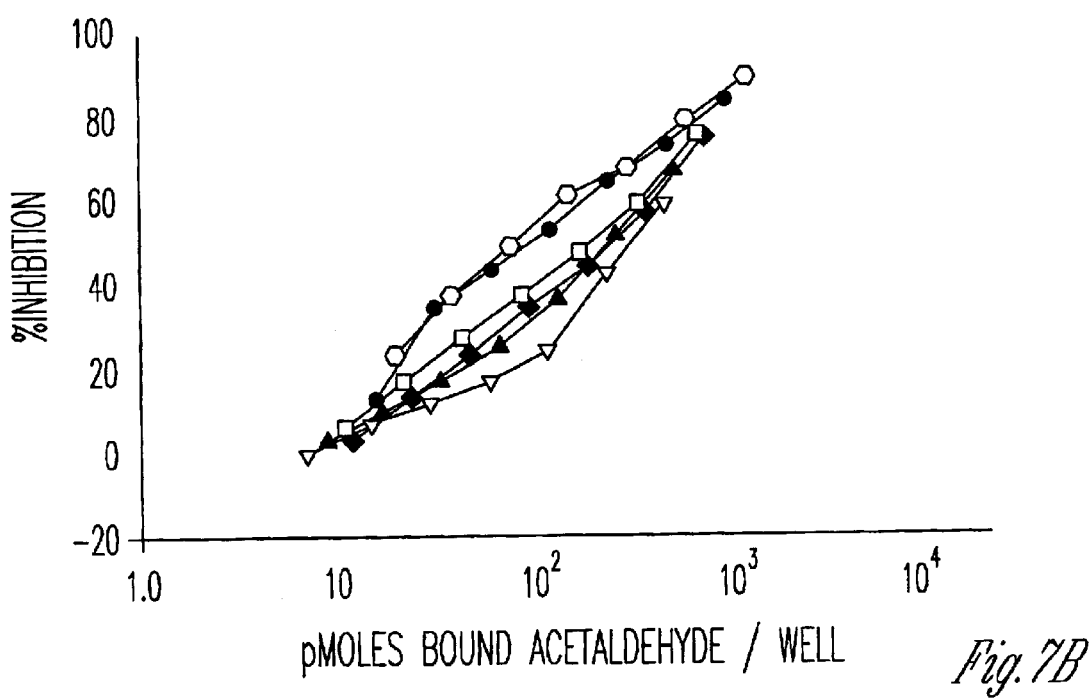

FIGS. 7(a) and 7(b) represent competitive ELISAs of lowly modified BSA-MAA adducts, using conditions of FIG. 5. Percent inhibition was determined based on nmoles of acetaldehyde bound per mg of BSA. 1.25 (hexagon); 1.00 (circle); 0.77 (square); 0.70 (diamond); 0.54 (triangle); and 0.48 (inverted triangle). 7(a) is percent inhibition in terms of protein concentration and 7(b) percent inhibition as a function of bound acetaldehyde.

Figure 8A:
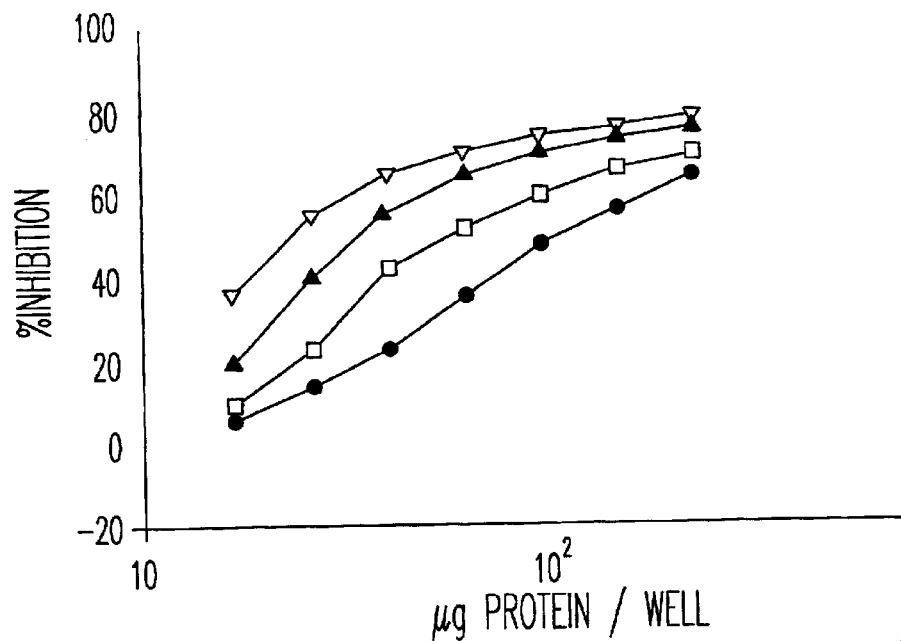

FIG. 8(a) is a graph depicting a competitive ELISA of lowly modified liver cytosolic protein-MAA adducts. Conditions were as in FIG. 6. Percent inhibition based on nmoles of acetaldehyde bound per mg of protein: 5.0 (inverted triangle); 2.5 (triangle); 1.1 (square); and 0.49 (circle). In 8(a) the percent inhibition is a plot as a function of protein concentration.

Figure 8B:
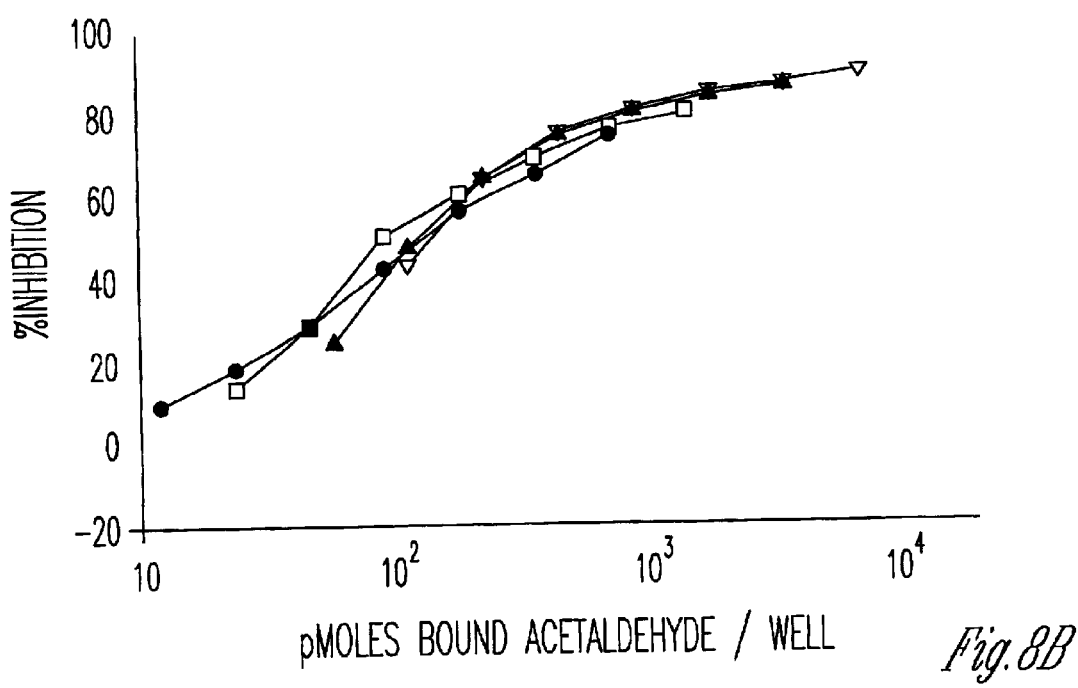

FIG. 8(b) is the data plotted as a function of bound acetaldehyde.

Figure 9A:
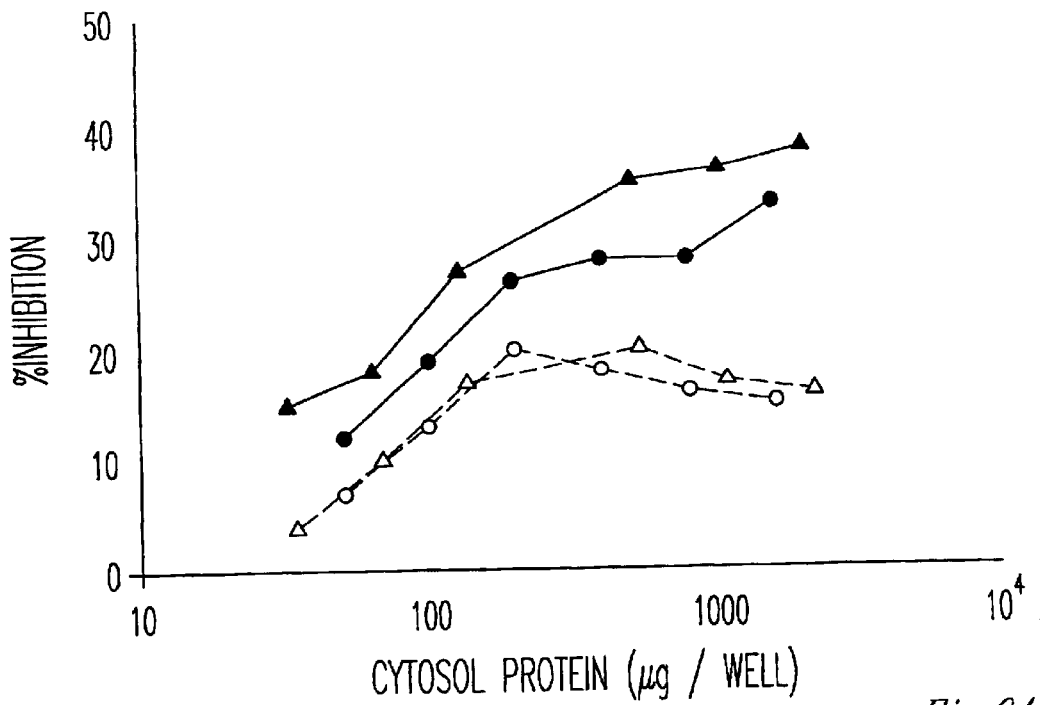

FIG. 9(a) depicts a competitive ELISA for detection of MAA adducts in liver cytosol from two ethanol-fed rats. Percent inhibition representing cytosol from ethanol fed rats (shaded triangle and circle) and their corresponding pair fed control (open circle and triangle).

Figure 9B:
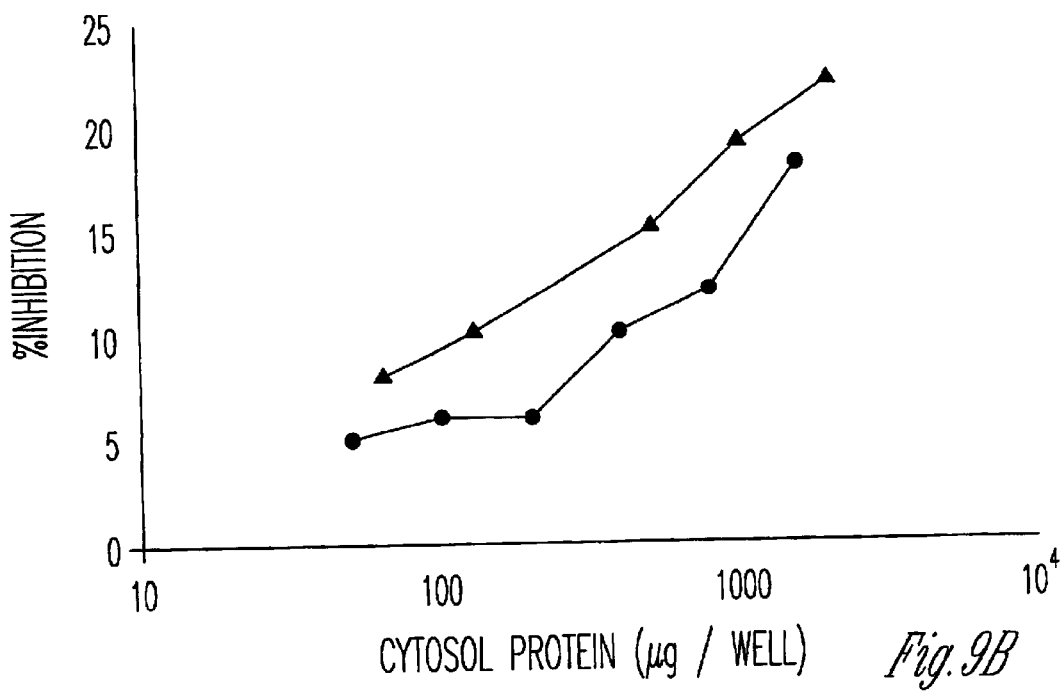

FIG. 9(b) represents the data from 9(a) with the control inhibition value subtracted.

DETAILED DESCRIPTION OF THE INVENTION

This invention relates to the discovery of a novel adduct present in the liver which is a hybrid of malondialdehyde and acetaldehyde. According to the invention these two products combine to form a highly immunogenic antigen adduct, denoted as malondialdehyde-acetaldehyde-adduct or (MAA). As used herein the term antigen shall encompass any foreign composition capable of illiciting an immune response and includes lipids, carbohydrates, peptides, proteins, or even ribo and deoxyribonucleic acids which contain an amino group. This novel protein adduct has been shown to be present in patients with alcohol liver disease and in rats chronically fed alcohol, and as such can serve as a marker for diagnosis, monitoring, and understanding the pathogenesis of liver diseases.

The novel hybrid adducts of the invention are formed at neutral standard conditions, both in vitro and in vivo. The adducts have the following formulas I and II:

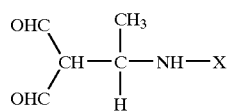

I.

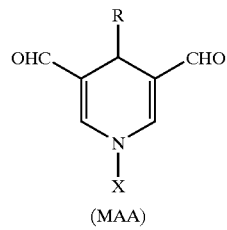

(MAA)

II.

Applicants have demonstrated that the presence of AA and MDA with proteins results in a dramatic increase in protein adduction, even at concentrations as low as 0.1 mM acetaldehyde and 0.2 mM malondialdehyde. Malondialdehyde and acetaldehyde together increased protein adduction 13 times that of acetaldehyde alone. Amino groups of proteins especially the $\epsilon$-amino group of internal lysines are the primary functional groups on which MAA forms.

Thus, the invention in one embodiment provides a novel hybrid adduct which is associated with alcohol liver disease and which may be detected as a marker of alcohol liver disease in biological samples obtained from animals. These adducts can be detected by use of antibodies generated to the novel hybrid malondialdehyde-acetaldehyde portion of the adduct or by other isolation and identification protocols. For example, the MAA hybrid adduct is highly fluorescent and the presence of MAA could be directly assayed from a biological sample using fluorescence detection.

As such, according to the invention, monoclonal and polyclonal antibodies that specifically react with the MAA adduct have been prepared. Experiments with these antibodies have shown that this protein adduct combination is present in patients with alcohol liver disease and in rats chronically fed alcohol. The monoclonal and polyclonal antibodies of the invention were obtained using methods standard in the art for production of such antibodies, and they do not react with acetaldehyde adducted proteins or malondialdehyde adducted proteins, indicating the formation of a new composition which is binding hepatic proteins.

Numerous studies in the literature have applied immuno chemical techniques to indicate the presence of a variety of protein adducts in the livers of ethanol treated animals as markers for alcohol liver disease. These would include acetaldehyde adducts, MDA adducts, and more recently hydroxyethyl radical-derived adducts. However, in most cases, the structural information and epitope characterization of the adducts are lacking, and quantitative data has not been reported.

In contrast, quantitative estimates for MAA adduct formation have been obtained according to the method of the invention and structure of MAA adducts has been delineated. Furthermore, as will be described more fully hereinafter, Applicants have discovered that MDA and acetaldehyde react together in a synergistic manner which suggest that the MAA adduct formation would be favored over other adducts formed with acetaldehyde or MDA alone and the MAA adducts likely represent the major species of adduct formed in the liver during ethanol metabolism in vivo. Novel protein adduct formation represents an event dependent on both mechanisms suggesting a common unifying process by which both mechanisms can contribute to a alcohol hepatoxicity.

The invention thus embodies a marker indicative of alcohol liver injury and a method of diagnosis, therapy or study of the same by assaying for the presence of this marker. The presence of this marker may be ascertained by collecting a biological sample which can include serum, plasma; urine and then using a variety of techniques known in the art to identify and/or quantify the marker's presence.

One method involves exploitation of the immunogenicity of the MAA-conjugate by developing monoclonal and polyclonal antibodies to all kinds of carrier proteins for use in immunological quantifications. In principle, all current immunoassays such as radioimmunoassay, enzyme immunoassay, fluorescence immunoassay, etc. are suitable for the immunological method and determination according to the present invention. In addition all variants of the procedure such as competitive immunoassay are applicable.

Polyclonal antibodies to the MAA adduct generally are raised in animals by multiple subcutaneous (sc) or intraperitoneal (ip) injections of the MAA protein adduct and an adjuvant. As is demonstrated herein, the MAA protein is highly immunogenic and can act as a carrier molecule for various antigens. In fact the MAA-adduct acts, as a specific immune enhancing factor, and works better than nonspecific adjuvants in generating high titer antibodies, so high IgG respons may be observed after fewer injections. Many antigens require separation of the protein and conjugation of it or of a fragment containing the amino sequence of the desired protein antigenic site to a second protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_g$, or $R^1N=C=NR$, where R and $R^1$ are different allyl groups. Quite unexpectedly, these types of protocols are not necessary for the antibodies of the invention as MAA itself causes the adducted protein to be highly immunogenic, theoretically by aiding in targeting, processing and/or presentation of the carrier protein to the humoral immune system. MAA also interacts with numerous proteins to form these highly immunogenic conjugates and has been shown to adduct with bovine serum albumin, human serum albumin, avalbumin, hen egg lysozyme, asialo glycoprotein receptor, rat liver microsomes, rat liver cytosol, human epidermal growth factor and mouse epidermal growth factor.

Under traditional procedures, animals ordinarily are immunized against the cells or immunogenic conjugates of MAA with monophosphoryl lipid A (MLP)/trehalose dicorynomycolate (TDM) (Ribi Immunochem. Research, Inc., Hamilton, Mont.) by injecting the solution intradermally at multiple sites. Two weeks later the animals are boosted with the original amount of conjugate in MPL/TDM. 7 to 14 days later animals are bled and the serum is assayed for anti MAA titer. Animals are boosted until the titer plateaus. Again, surprisingly, the MAA-protein adduct is so immunogenic it can generate a IgG response in as little as 3 days, and adjuvants such as MPL/trehalose dicorynomycolate (TDM), or Freunds may not be necessary.

Monoclonal antibodies are prepared by recovering spleen cells from immunized animals and immortalizing the cells in conventional fashion, e.g. by fusion with myeloma cells or by Epstein-Barr (EB)-virus transformation and screening for clones expressing the desired antibody. The hybridoma technique described originally by Koehler and Milstein, Eur. J. Immunol., 6:511 (1976) and also described by Hammerling et al., in "Monoclonal Antibodies and T-Cell Hybridomas, Elsevier, N.Y., pp. 563–681 (1981) both of which are expressly incorporated herein by reference has been widely applied to produce hybrid cell lines that secrete high levels of monoclonal antibodies against many specific antigens.

The hybrid cell lines can be maintained in vitro in cell culture media. The cell lines producing the antibodies can be selected and/or maintained in a medium containing hypoxanthine-aminopterin thymidine (HAT). In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion-exchange chromatography, affinity chromatography such as protein A/protein G column chromatography, and the like. The antibodies described herein are also recovered from hybridoma cell cultures by conventional methods such as precipitation with 50% ammonium sulfate. The purified antibodies can then be sterile filtered.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. All monoclonal and polyclonal antibodies including hybridomas are maintained at the VA Medical Center in Omaha, Nebr.

The monoclonal antibodies herein also include hybrid and recombinant antibodies produced by splicing a variable (including hypervariable) domain of an anti-MAA antibody with a constant domain (e.g. "humanized" antibodies), or a light chain with a heavy chain, or a chain from one species with a chain from another speci s, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g. Cabilly, et al., U.S. Pat. No. 4,816,567; Mage & Lamoyi, in "Monoclonal Antibody Production Technique and Applications", pp. 79–97 (Marcel Dekker, Inc., New York, 1987).)

Thus, the modifier "monoclonal" indicates the character of the antibody as being obtained from a substantially homogenous population of antibodies, and is not to be construed as requiring production of the antibody by any particular method. For example, the monoclonal antibodies to be used in accordance with the present invention may be made by the hybridoma method described by Kohler a Milstein, supra, or may be made by recombinant DNA methods (Cabilly, et al., supra).

Diagnostic Uses of MAA and Anti-MAA Antibodies

Anti-MAA antibodies are useful in diagnostic assays for MAA expression in specific cells or tissues wherein the antibodies are labeled as described below and/or are immobilized on an insoluble matrix. Anti-MAA antibodies also are useful for the affinity purification of the MAA from recombinant cell culture or natural sources. The Anti-MAA antibodies that do not detectably cross-react with other protein or materials, can be used to purify each MAA conjugated protein adduct free from other homologous receptors.

Suitable diagnostic assays for the MAA are well known per se. For example, a biological sample may be assayed for MAA by obtaining the sample from a desired source, admixing the sample with anti-MAA antibody to allow the antibody to form antibody/MAA complex with any MAA present in the mixture and detecting any antibody/MAA complex present in the mixture. The biological sample may be prepared for assay by methods known in the art which are suitable for the particular sample. The methods of admixing the sample with antibodies and the methods of detecting antibody/MAA complex are chosen according to the type of assay used. Such assays include competitive and sandwich assays, and steric inhibition assays. Competitive and sandwich methods employ a phase-separation step as an integral part of the method while steric inhibition assays are conducted in a single reaction mixture.

Analytical methods for the MAA all use one or more of the following reagents: labeled MAA analogue, immobilized MAA analogue, labeled anti-MAA antibody, immobilized anti-MAA antibody and steric conjugates. The labeled reagents also are known as "tracers." As will be demonstrated, MAA itself is highly fluorescent and may be directly assayed without labeling.

The label used may be any detectable functionality that does not interfere with the binding of MAA and anti-MAA antibody. Numerous labels are known for use in immunoassay, xamples including moi ties that may be detected directly, such as fluorochrome, chemiluminescent, and radioactive labels, as well as moieties, such as enzymes, that must be reacted or derivatized to be detected. Examples of such labels include the radioisotopes $^{33}P$, $^{14}C$, $^{125}I^3H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbondiamides, dimaleimides, bisimidates, bis-diazotized benzidine, and the like may be used to tag the antibodies with the above-described fluorescent, chemiluminescent, and enzyme labels. See, for example, U.S. Pat. No. 3,940,475 (fluorometry) and U.S. Pat. No. 3,645,090 (enzymes); Hunter et al., Nature, 144:945(1962); David et al., Biochemistry, 13:1014–1021 (1974); Pain et al., J. Immunol. Methods, 40:219–230 (1981); and Nygren, J. Histochem. and Cytochem., 30:407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See, for example, O'Sullivan et al., "Methods for the Preparation of Enzyme-Antibody Conjugates for Use in Enzyme Immunoassay", in Methods in Enzymology, et. J. J. Langone and H. Van Vunakis, Vol. 73 (Academic Press, New York, N.Y., 1981), pp. 147–166.

Immobilization of reagents is required for certain assay methods. Immobilization entails separating the anti-MAA antibody complexes from any MAA that remains free in solution. This conventionally is accomplished by either insolubilizing th anti-MAA antibody or MAA analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-MAA antibody or MMA analogue afterward, e.g., by immunoprecipitation.

Other assay methods, known as competitive or sandwich assays, are well established and widely used in the commercial diagnostics industry.

Competitive assays rely on the ability of a tracer MAA analogue to compete with the test sample MAA for a limited number of anti-MAA antibody antigen-binding sites. The anti-MAA antibody generally is insolubilized before or after the competition and then the tracer and MAA bound to the anti-MAA antibody are separated from the unbound tracer and MAA. This separation is accomplished by decanting (where the binding partner was preinsolubilized) or by centrifuging (where the binding partner was precipitated after the competitive reaction). The amount of test sample MAA is inversely proportional to the amount of bound tracer as measured by the amount of marker substance. Dose-response curves with known amounts of MAA are prepared and compared with the test results to quantitatively determine the amount of MAA present in the test sample. These assays are called ELISA Systems when enzymes are used as the detectable markers.

Another species of competitive assay, called a "homogeneous" assay, does not require a phase separation. Here, a conjugate of an enzyme with the MAA is prepared and used such that when anti-MAA antibody binds to the MAA the presence of the anti-MAA antibody modifies the enzyme activity. In this case, the MAA or its immunologically active fragments are conjugated with a bifunctional organic bridge to an enzyme such as peroxidase. Conjugates are selected for use with anti-MAA antibody so that binding of the anti-MAA antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small MAA fragment so that antibody to hapten is substantially unable to bind the conjugate at the same time as anti-MAA antibody. Under this assay procedure the MAA present in the test sample will bind anti-MAA antibody, thereby allowing anti-hapten to bind the conjugate, resulting in a change in the character of the conjugate hapten, e.g., a change in fluorescence when the hapten is a fluorophore.

Sandwich assays particularly are useful for the determination of MAA or anti-MAA antibodies. In sequential sandwich assays an immobilized anti-MAA antibody is used to adsorb test sample MAA, the test sample is removed as by washing, the bound MAA is used to adsorb a second, labeled anti-MAA antibody and bound material is then separated from residual tracer. The amount of bound tracer is directly proportional to test sample MAA. In "simultaneous" sandwich assays the test sample is not separated before adding the labeled anti-MAA. A sequential sandwich assay using an anti-MAA monoclonal antibody as one antibody and a polyclonal anti-MAA antibody as the other is useful in testing samples for MAA.

The foregoing are merely exemplary diagnostic assays for MAA. Other methods now or hereafter developed that use anti-MAA antibody for the determination of MAA are included within the scope hereof, including the bioassays described above.

All references cited in this specification are hereby expressly incorporated by reference. The following examples are offered by way of illustration and not by way of limitation.

EXAMPLE 1

Preparation of MAA Polyclonal Antibody

Materials

Acetaldehyde (5 mCi/mmole) was purchased from New England Nuclear (Boston, Mass.). Radiolabeled acetaldehyde was received from the manufacturer frozen as an aqueous solution (1 mCi/ml), thawed and diluted to 250 $\mu$Ci/ml with distilled water, rapidly refrozen, and stored at −70° C. The specific activity of the acetaldehyde was checked as described by Miwa et al., "The Direct Oxidation of Ethanol by a Catalase- and Alcohol Dehydrogenase-Free Reconstituted System Containing Cytochrome P-450", Arch Biochem Biophys, 1978; 30:464–475. Bovine serum albumin (BSA) (crystallized, lyophilized, and fatty acid free) was obtained from Sigma Chemical Co. (St. Louis, Mo.). Nonradioactive acetaldehyde was purchased from Aldrich Chemical Co. (Milwaukee, Wis.). MDA was obtained as the sodium salt (MDA.Na) by treatment of tetramethoxypropane (Aldrich) with NaOH according to the method of Kikugawa and Ido. "Studies on Peroxidized Lipids. V. Formation and Characterization of 1,4-Dihydrophyridine-3, 5-Dicarbaldehydes as Model of Fluorescent Components in Lipofusion", Lipids, 1984; 19:600–608. All other chemicals were of analytical grade.

Determination of Stable Binding of Acetaldehyde to Proteins in the Presene of MDA Concentrations of acetaldehyde (0.1 mM or 1.0 mM) were incubated with various protein solutions in the absence and presence of varying concentrations of MDA. Incubations were conducted in phosphate buffer (0.1 M, pH 7.4) at 37° C. in polypropylene vessels that were sealed to minimize the loss of volatile radioactivity. The reactions were performed under nitrogen gas in the dark. During a 72-hr incubation period, aliquots were removed for stable acetaldehyde binding determinations and fluorescence measurements as previously described. Hoffmann, "Reaction of Acetaldehyde with Proteins: Formation of Stable Fluorescent Adducts", Alcohol Clin Exp Res, 1993; 17:69–74. Briefly, postincubation, free and unstable-bound acetaldehyde were separated by exhaustive dialysis against phosphate buffer for 24 hours at 4° C. Radioactivity was then measured in the retenate and represented stably bound acetaldehyde. Results are expressed as nmoles acetaldehyde bound per mg of protein. Fluorescence measurements were obtained on postdialysis samples using a Perkin Elmer LS-5B spectrophotofluorometer attached to a Perkin Elmer GP-100 graphics printer.

Preparation, Purification and Biotinylation of Rabbit Polyclonal Antibody to MDA/Acetaldehyde-Modified Proteins The immunogen was prepared by the treatment of rabbit plasma proteins (prepared by ammonium sulfate precipitation) Klassen, "Detection of Reduced Acetaldehyde Protein Adducts Using a Unique Monoclonal Antibody", Alcohol Clin Exp Res, 1994; 18:164–171) at a concentration of 1 mg/ml with 1 mM acetaldehyde plus 1 mM MDA for 3 days at 37° C. Following overnight dialysis against 0.1 M phosphate buffer (pH 7.4 and 4° C.), the solution was mixed with an equal volume of Freund's complete adjuvant and emulsified. New Zealand white rabbits were injected subcutaneously in four sites along their backs (400 $\mu$g of modified protein). After two and four weeks, the rabbits were boosted by the same procedure except Freund's incomplete adjuvant was used. Two weeks after the final injection, serum was obtained and tested for antibody activity.

The resulting antisera was then affinity purified. Lysine derivatized Sepharose 4B beads (Sigma Chemical Co., St. Louis, Mo.) were modified by adding acetaldehyde (1 mM) and MDA (1 mM) in 0.1 phosphate buffer, pH 7.4, and incubating at 37° C. for 3 days with constant shaking. The beads were washed with four volumes of buffer and poured into a 0.7 cm×15 cm low pressure Econo-Column (Bio-Rad Laboratories, Hercules, Calif.). Ten ml of rabbit serum from the immunized animals were loaded onto the column. The column was washed with 5 volumes of buffer, followed by 1 M NaCl, and then eluted with 0.5 M acetic acid (pH 2.5) into Tris buffer (pH 8.2) to neutralize the acid. The eluted material was further purified by Protein G-Sepharose B (Pharmacia, Piscataway, N.J.) column chromatography, yielding a purified IgG fraction of greater than 95%.

The affinity purified antibody was biotinylated by the method of Bayer and Wilchek. Bayer, "The Use of the Avidin-Biotin Complex as a Tool in Molecular Biology", Methods Biochem Anal, 1980; 26:1–46. Briefly, the antibody at 1 mg/ml was dialyzed against 0.1 M sodium borate buffer (pH 8.8) for 4 hours at room temperature. N-hydroxysuccinimide biotin (100 $\mu$g) (Sigma Chemical Co., St. Louis, Mo.) was added to this solution and incubated at room temperature for four hours. After this time, the solution was treated with 15 $\mu$l of 1 M ammonium chloride for 10 minutes at room temperature, and dialyzed overnight at 4° C. against phosphate buffered saline (PBS)(pH 7.4). The biotinylated antibody was stored at 4° C. until use.

EXAMPLE 2

Direct and Competitive Enzyme-Linked Immunosorbent Assays (ELISA)

A direct ELISA was used to screen the polyclonal rabbit antiserum and ascertain the specificity of the affinity purified antibody. Test proteins were diluted to 20 $\mu$g/ml in bicarbonate buffer (pH 9.6), and 100 $\mu$l of sample were added to a 96-well ELISA plate (Immulon IV, Nunc, Fisher Scientific, St. Louis, Mo.). After incubation at 37° C. for 1 hour followed by an overnight incubation at 4° C., the coated wells were washed with PBS containing 0.05% Tween-20 (PBST) to remove unbound protein. The biotinylated antibody was then added to the antigen coated wells and incubated at 37° C. for 1 hour. After washing 3 times with PBST, 100 $\mu$l of alkaline phosphatase-conjugated streptavidin (Zymed Laboratories, San Francisco, Calif.) were added, and incubated at room temperature for 10 minutes. The plates were then washed three times with PBST, and 100 $\mu$l of the substrate, p-nitrophenyl phosphate (Sigma), were added. Optical density at 405 nm was measured by a Dynatech Micro ELISA Reader MR7000 (Dynatech, Chantilly, Va).

A competitive ELISA was developed in order to detect the presence and to quantify the level of MDA/acetaldehyde modified proteins. Following the basic methodology developed by Roberts, et al, "A Sensitive Immunochemical Assay for Acetaminophen-Protein Adducts", J Pharmacol Exp Ther, 1987; 241:527–533; Pumford, et al, "Immunochemical Quantitation of 3-(cystein-S-yl)Acetaminophen Adducts in Serum and Liver Proteins of Acetaminophen-Treated Mice", J Pharmacol Exp Ther, 1989; 248:190–196, incorporated herein by reference, these assays were conducted by allowing a limiting amount of antibody to react with inhibitor, either standard or unknown, in the presence of excess solid phase antigen (MDA/acetaldehyde modified proteins). After preliminary experiments, the following specific and optimal conditions were established to conduct the competitive ELISA assay: ELISA plate wells were coated with 100 μl of BSA that had been treated with 1 mM acetaldehyde and 1 mM MDA for 24 hours (approx. 2 μg/well). Biotinylated antibody (1/500 final dilution) was incubated with varying concentrations of test samples (standards or unknowns) overnight at 4° C., and then a 100 μl-aliquot of each sample was added to duplicate wells of the coated plates and incubated for 45 minutes at 37° C. After washing, 100 μl of alkaline phosphatase-conjugated streptavidin was added, and procedures as described above for the Direct ELISA were used to obtain optical density measurements. Results for each inhibitor concentration were expressed as % inhibition which was calculated using the following formula developed by Roberts et al (supra).

$$\% \text{ Inhibition} = (OD_{max} - BKG) - (OD_{sample} - BKG) \times 100(OD_{max} - BKG)$$

where $OD_{max}$ is OD in the absence of inhibitor, BKG is OD from nonspecific absorption of assay reagents and $OD_{sample}$ is the OD for a given concentration of standard or unknown sample.

Preparation of Liver Cytosol from Ethanol-Fed and Control Rats

Male Wistar Rats (150–160 g) were pair-fed the Lieber-DeCarli ethanol-containing and the control liquid diets, Lieber, et al., "The Feeding of Ethanol in Liquid Diets", 1986 Update, Alcohol Clin Esp Res, 1986; 10:550–553, incorporated herein by reference, for up to 5 weeks according to the methods in Casey, et al., "Chronic Ethanol Administration Impairs the Binding and Endocytosis of Asialoorosomucoid in Isolated Hepatocytes", J Biol Chem, 1987; 262:2704–2710, also incorporated herein. Isolated hepatocytes were prepared by collagenase perfusion as previously reported, and an hepatocyte cytosolic fraction was prepared by ultracentrifugation. Volentine, et al., Subcellular Location of Secretory Proteins Retained in the Liver During the Ethanol-Induced Inhibition of Hepatic Protein Secretion in the Rat", Gastroenterology, 1986; 90:158–165. Protein content of the cytosol fraction was determined by the method Lowry et al., "Protein Measurement with the Folin Phenol Reagent", J Biol Chem, 1951; 193:265–275. Aliquots of hepatocyte cytosolic proteins were analyzed for adducts by competitive ELISA on the same day of preparation.

Figure 1:
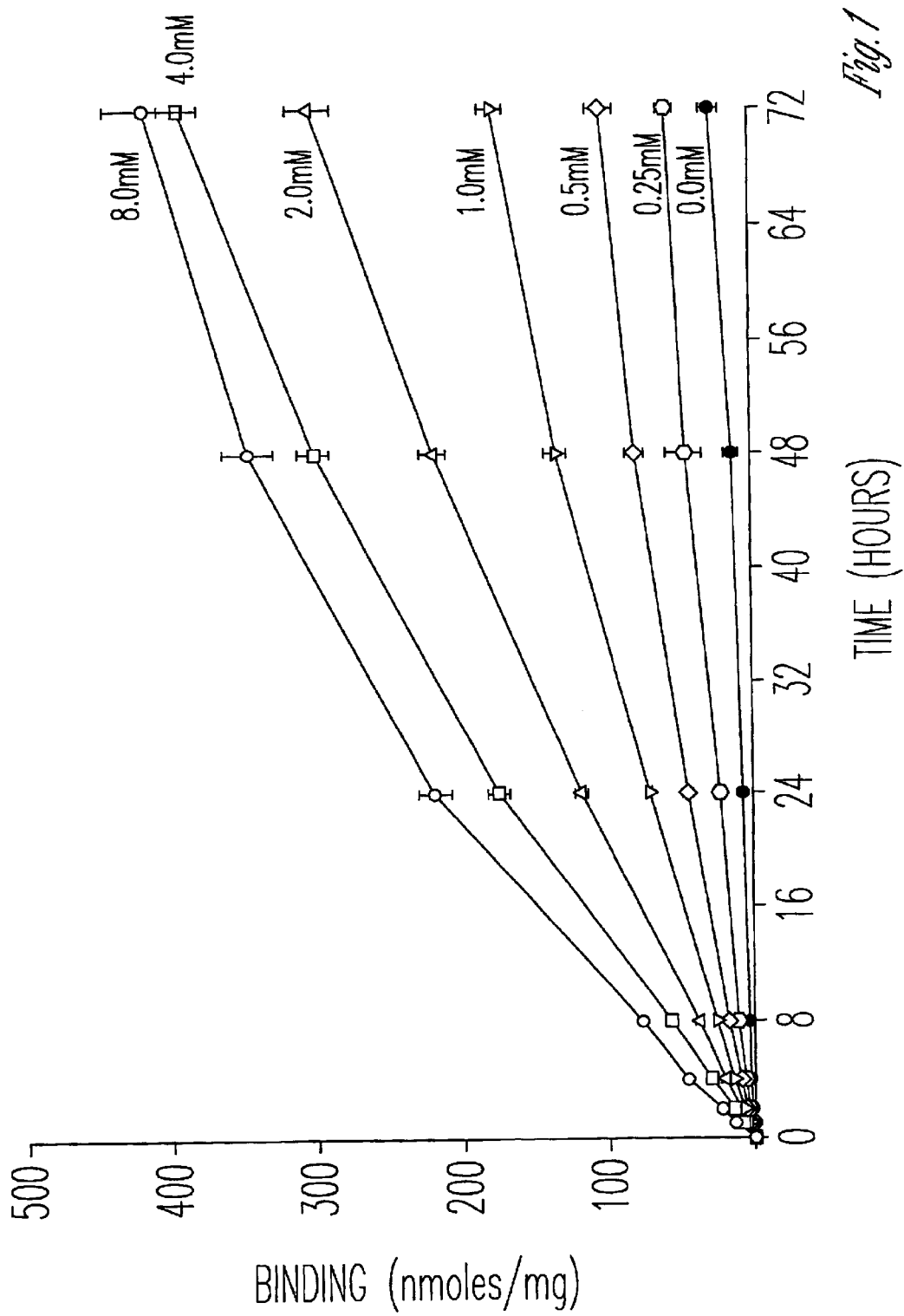
FIG. 1 is a graph demonstrating the synergistic action of MDA and acetaldehyde on the binding of bovine serum albumin (BSA). The graph depicts varying concentrations of MDA incubated in the presence of acetaldehyde (1 mM) over a 72-hour time course. Thus MDA markedly simulates the binding of acetaldehyde to BSA in a concentration dependent manner. Results are expressed as mean±SE for five experiments.
Figure 2:
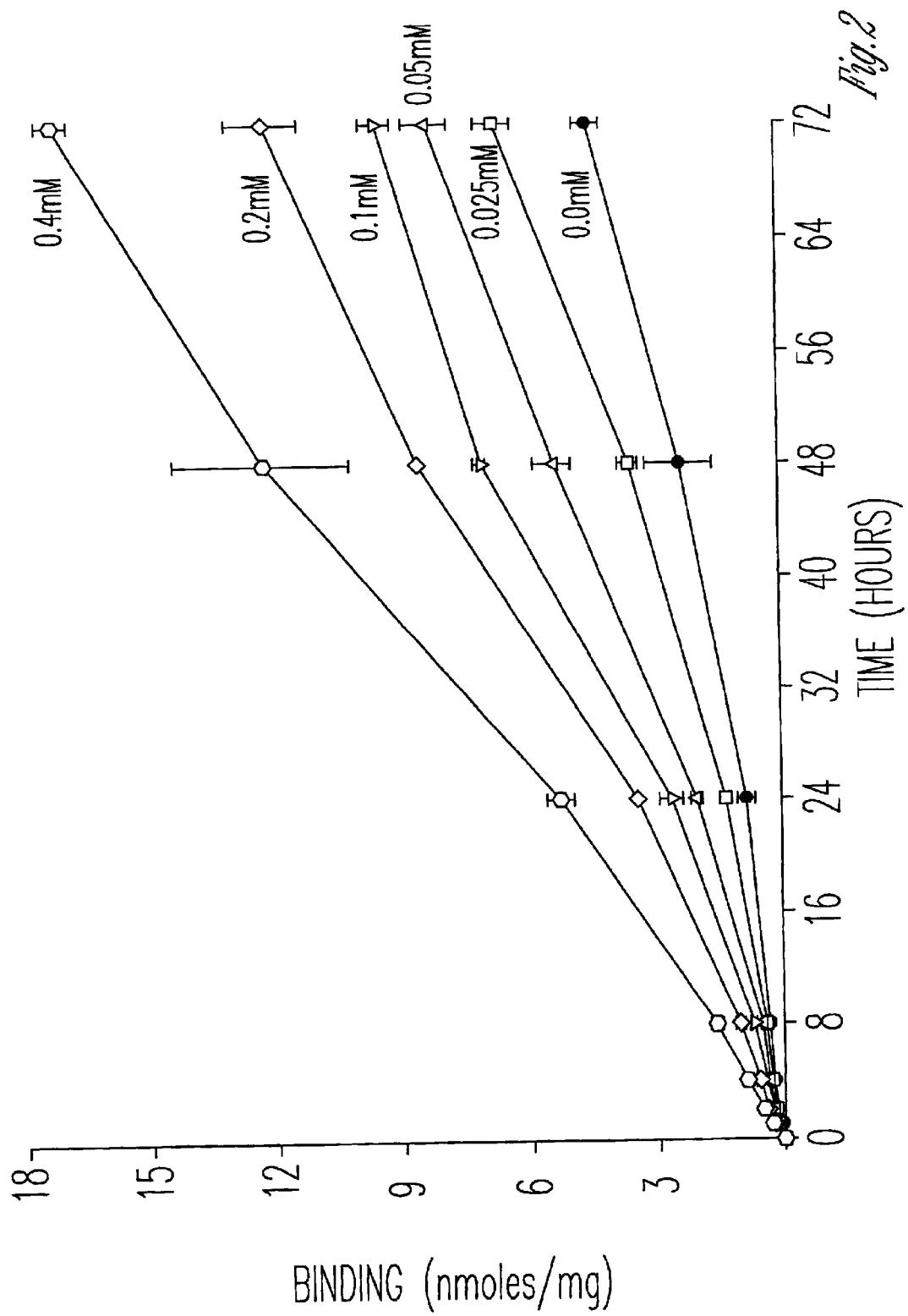
FIG. 2 is a graph depicting the stability of the interaction between acetaldehyde and MDA. The graph depicts acetaldehyde at 0.1 mM incubated with BSA 1 mg/ml at 37° C. in the absence and presence of MDA (0.2 to 0.4 mM) over 72 hours and there was still a synergistic effect. Results and mean+SE for four experiments.

The results illustrated in FIG. 1 demonstrate the dramatic effects of MDA on the stable binding of acetaldehyde to BSA. When acetaldehyde (1 mM) was incubated with bovine serum albumin (BSA) in the presence of varying concentrations of MDA over a 72-hour time course, MDA markedly stimulated the binding of acetaldehyde to BSA in a concentration-dependent manner. For example, after 24 hours of incubation, a 13-fold stimulation at a 4-fold molar excess of MDA were observed. It appeared that maximum stimulation of acetaldehyde binding occurred at about a 4 molar excess of MDA. The MDA-induced increase in acetaldehyde binding to BSA also was observed when lower concentrations of aldehydes were used. When acetaldehyde at 0.1 mM was incubated with MDA (0.1 to 0.4 mM), the MDA-stimulation of acetaldehyde binding to BSA was still apparent although the effect was somewhat attenuated at these lower concentrations (FIG. 2). In addition to BSA, other proteins that were tested also exhibited markedly enhanced binding to acetaldehyde in the presence of MDA. These included mouse plasma proteins, rabbit plasma proteins, hemoglobin, epidermal growth factor, polylysine and rat liver cytosol proteins.

Fluorescence of MDA-AA Adducts

Figure 3A:
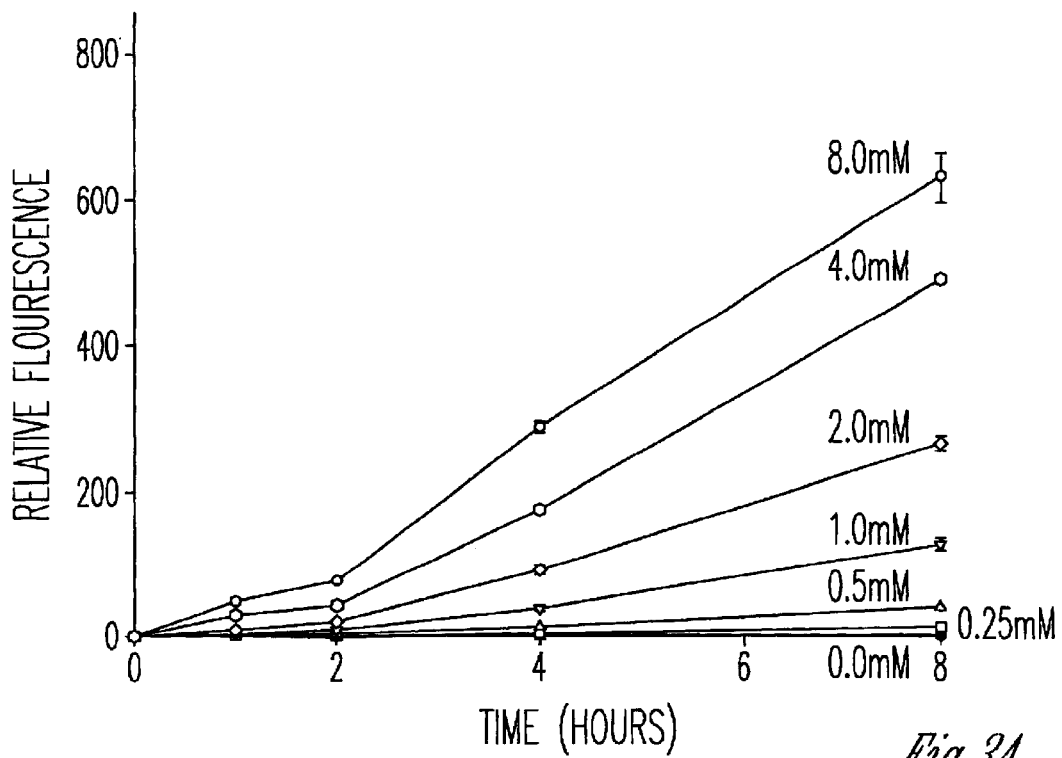
FIGS. 3(a) and (b) depict fluorescence intensities of reaction mixtures of BSA with acetaldehyde and MDA.
Figure 3B:
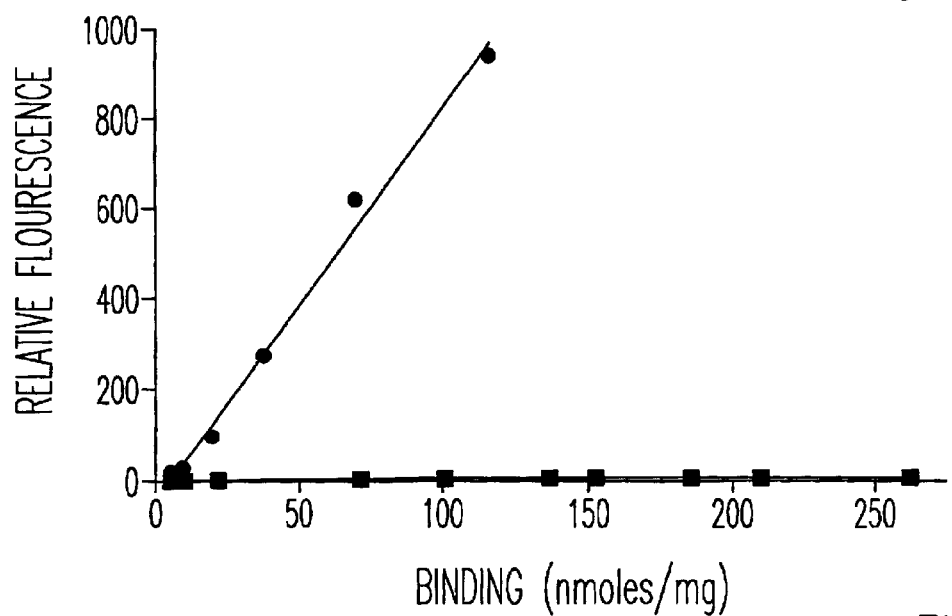
FIG. 3(b) is a graph depicting the relationship of acetaldehyde binding and fluorescence in the absence (square) and presence (circle) of MDA. Reaction mixtures with MDA exhibited an absorption maximum at 460 nm and in the absence of MDA the excitation and emission maxima was 357 nm and 440 nm, respectively.

The stimulation of acetaldehyde binding to BSA by MDA was accompanied by the formation of highly fluorescent products (FIG. 3A). Although previous studies have shown that reaction mixtures of BSA and high concentrations of acetaldehyde (<3 mM) alone also exhibited fluorescent properties, fluorescence observed in the presence of MDA was distinctly different. As shown in FIG. 3B, acetaldehyde binding in the presence of MDA resulted in the formation of extremely highly fluorescent products compared to the fluorescence associated with equivalent binding seen with acetaldehyde alone. In addition, the excitation and emission maxima were different for the two conditions (FIG. 3). When BSA was treated with MDA alone, fluorescence was also apparent, but was about 20–60 fold less over the MDA concentration ranges tested (0 to 8.0 mM) than that observed when acetaldehyde and MDA were both present. Thus, the stimulation of acetaldehyde binding to proteins by MDA is due to th formation of distinct products that differ from the products formed when proteins are treated with ither acetaldehyde or MDA along, a MDA-acetaldehyde adduct (MAA).

Figure 4A:
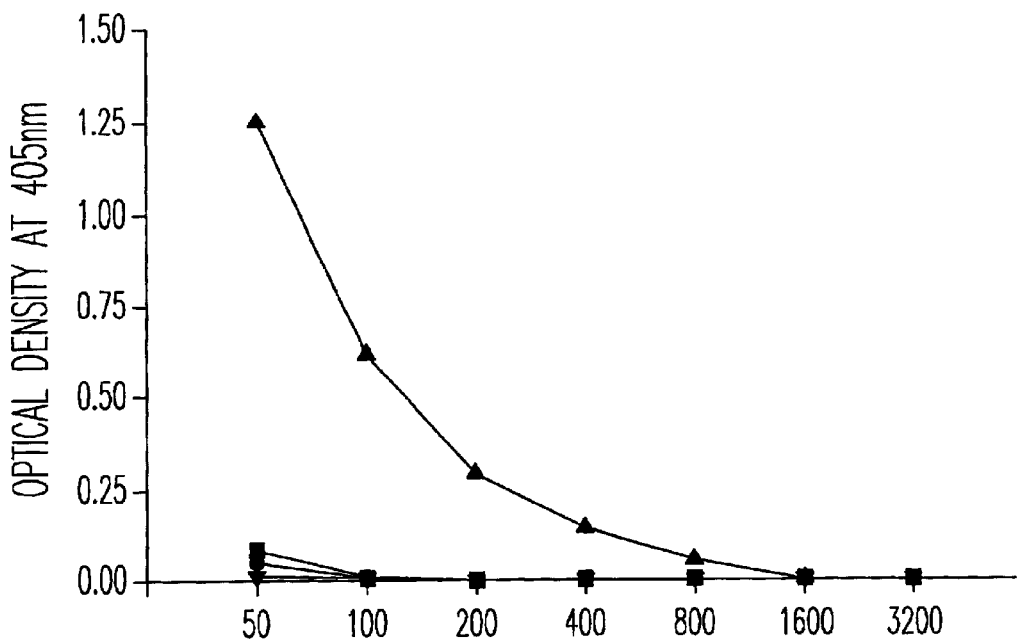
FIGS. 4(a) and 4(b) represent direct ELISA of the polyclonal antibodies generated from rabbit injected with plasma protein-MAA conjugates against BSA-aldehyde conjugates to the MAA-BSA conjugate or unmodified BSA.
Figure 4B:
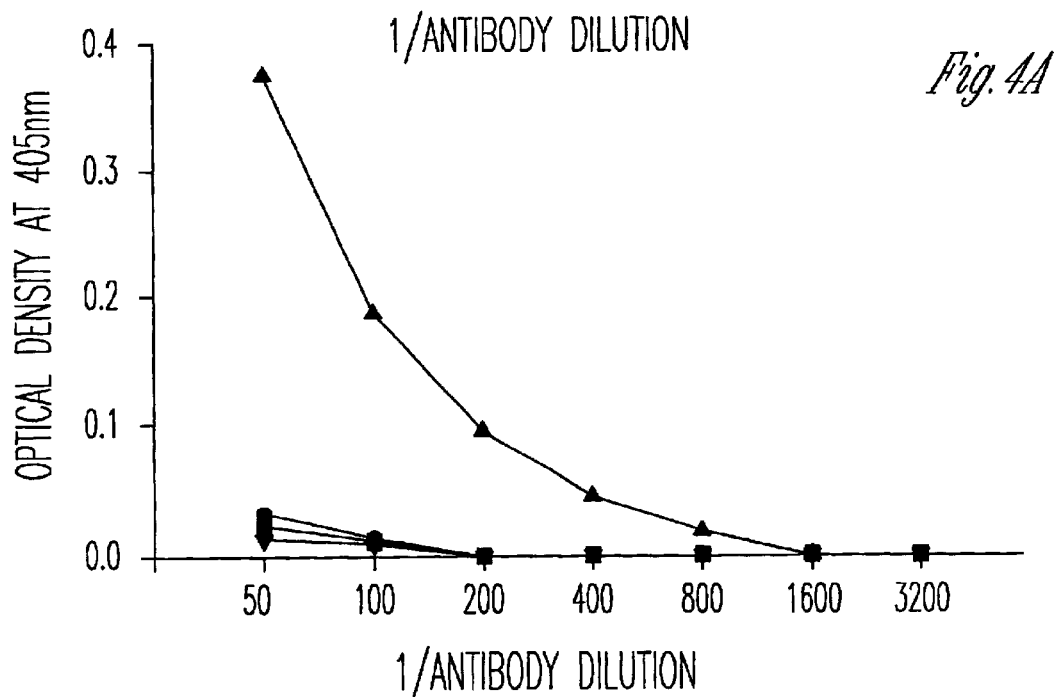

In subsequent experiments, an immunoassay was developed in order to detect the presence of MAA adducts in liver samples. A rabbit antibody was raised against the MAA adduct by immunizing the animals with rabbit plasma proteins-MAA adducts, and by purifying the antiserum in order to obtain an affinity purified IgG fraction that would recognize MAA adducts. The specificity of this antibody was tested by a direct ELISA against modified and unmodified BSA. The antibody recognized only BSA modified with MAA. The antibody had affinity for BSA modified with either 1 mM or 0.1 mM concentrations of both the aldehydes (FIG. 4). The antibody did not recognize native (unmodified) BSA or BSA modified with either acetaldehyde or MDA alone (FIG. 4). The specificity for MAA adducts was further tested with other proteins (e.g. rabbit plasma proteins, mouse plasma proteins, hemoglobin), and ELISA again demonstrated, as was the case with BSA, that this affinity purified antibody specifically recognized MAA epitopes on proteins.

Figure 5A:
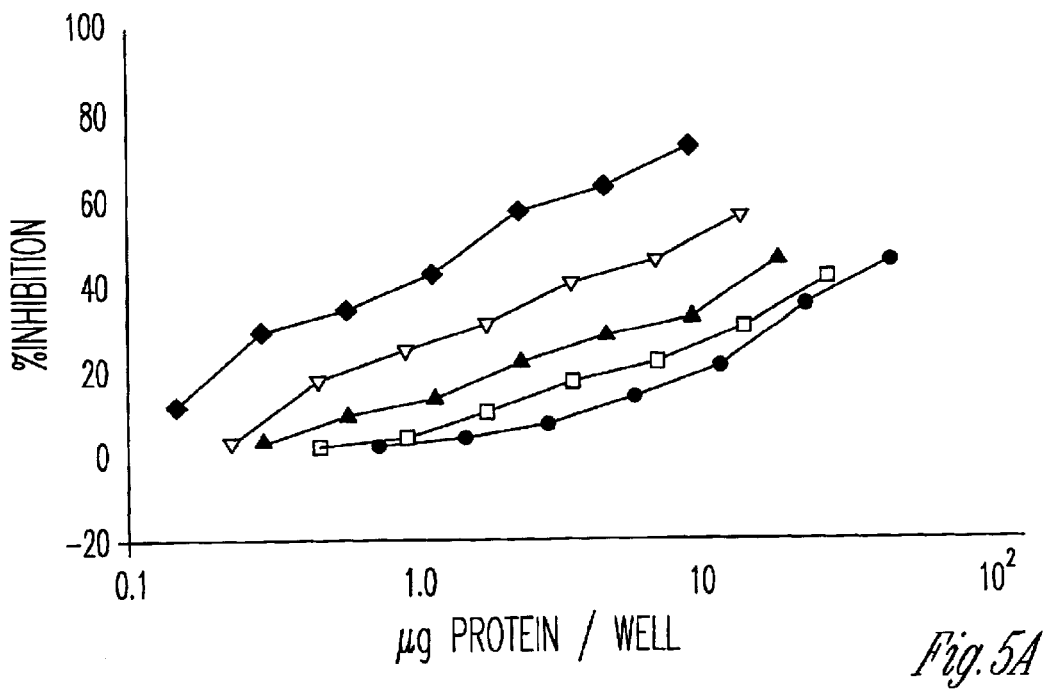
FIGS. 5(a) and 5(b) are graphs depicting the result of a competitive ELISA for competitive inhibition of BSA-MAA adducts, and the ability of variously MAA-modified BSA's to inhibit antibody binding. BSA was derivatized with varying concentrations of MDA and acetaldehyde and stable binding of acetaldehyde was quantified. Degree of modification based on nmoles of acetaldehyde bound per mg of BSA were 28 (diamond); 15.4 (inverted triangle); 19.1 (triangle); 6.0 (square); and 3.5 (circle).
Figure 5B:
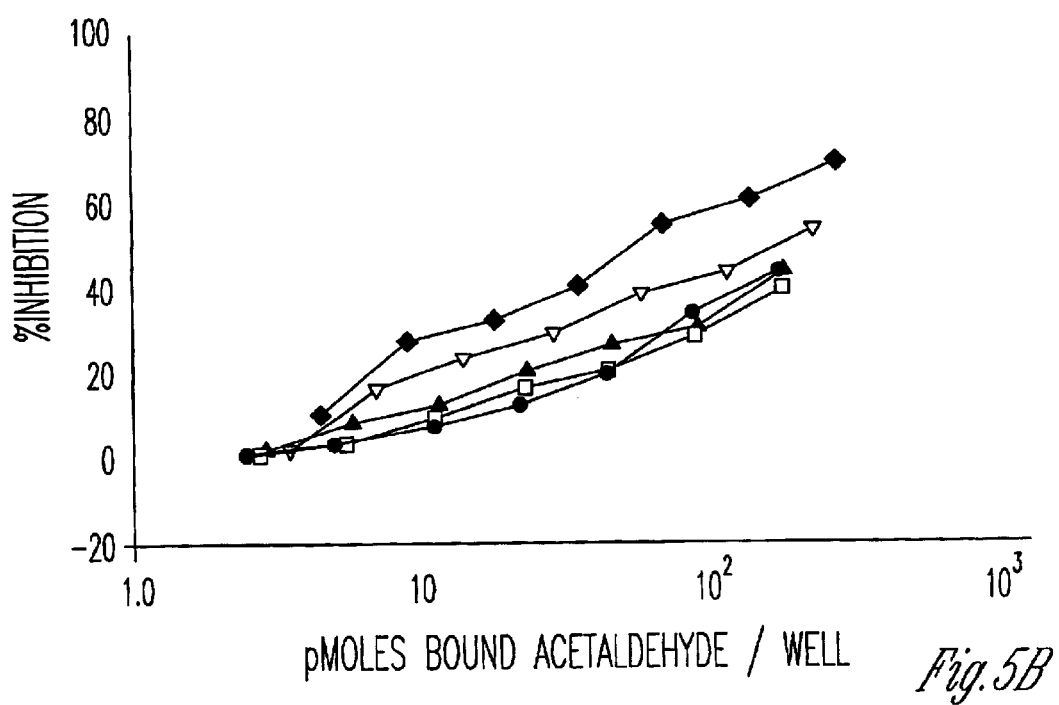

This affinity purified antibody was then used in the development of a competitive ELISA in order to detect and quantify MAA adducts in liver samples. The applicability of this method was tested by preparing BSA at various levels of MAA derivatization. The substitution level of each modified BSA was determined by $^{14}C$ radiolabeling, and the values on the level of MAA substitution were expressed as nmoles of acetaldehyde bound per mg of BSA. When these BSA-MAA adducts were tested in the competitive ELISA, the results showed an ordered family of inhibition curves where the most highly modified BSAs were the most efficient inhibitors, and the least substituted BSAs were the least efficient inhibitors when the % inhibitions were plotted as a function of BSA concentrations (FIG. 5A). On the other hand, when the same inhibition data were plotted as a function of MAA modification (i.e. acetaldehyde bound), the family of curves tended to become superimposed (FIG. 5B). These results indicated that the competitive ELISA could adequately estimate the level of MAA modification of proteins, and the number of MAA epitopes appeared to be the most important determining factor in causing inhibition of antibody binding. It should be pointed out, however, that under these conditions, inhibitions produced by MAA epitopes appeared to be more efficient in the more highly substituted BSAs (FIG. 5B). When the above experiments were repeated except that liver cytosol proteins were modified with MAA, similar inhibition curves were obtained as those observed for BSA-MAA (FIG. 6). In addition, native (untreated) liver cytosol proteins and liver cytosol proteins treated with MDA or acetaldehyde alone caused minimal to no inhibitions of antibody binding in the competitive ELISA. These results indicate the applicability of the competitive ELISA to detect and quantify MAA adducts in liver cytosol proteins, and similar procedures can be used to test other antibodies.

EXAMPLE 3

Further, experiments were conducted in order to verify the use of the competitive ELISA in the quantification of lowly modified MAA proteins. The data shown in FIGS. 5 and 6 indicated the number of MAA epitopes (i.e. acetaldehyde binding) that was necessary to be present in the assay mixture to produce sufficient inhibition of antibody binding in the competitive ELISA. Based upon the consideration of these data, the analysis of a large sample size (mg range) in the competitive ELISA for minimally modified proteins was dictated. In this case, when percent inhibition was plotted as a function of protein concentration, a family of inhibition curves were generated showing increased inhibition efficiencies with increasing degrees of MAA modification for both BSA-MAA (FIG. 7A) and liver cytosol proteins-MAA (FIG. 8A). However, when the inhibition data was plotted as a function of the number of MAA epitopes (i.e. acetaldehyde binding), the family of curves were superimposed for both the BSA-MAA (FIG. 7B) and liver cytosol proteins-MAA (FIG. 8B). These results confirmed the applicability of the competitive ELISA for the use of detecting and quantifying MAA epitopes on liver cytosol proteins.

The results of competitive ELISA in liver cytosol from two rats that were fed ethanol for 5 weeks and their corresponding pair-fed controls are shown in FIG. 9. MAA adducts were readily detected in the ethanol-fed rats as indicated by the inhibition curves for the liver cytosol obtained from these two ethanol-fed rats. Cytosol from control livers appeared to show only slight nonspecific inhibitions (FIG. 9A), and when these inhibition values were subtracted from the corresponding values from the ethanol-fed rats, inhibition curves were generated that represented an estimation of the quantity of MAA modifications of liver cytosol proteins from the ethanol-fed animals (FIG. 9B). Competitive ELISA assays were then conducted on liver cytosolic proteins from seven ethanol-fed rats and their corresponding pair-fed controls. When the inhibition curves gen rated by liver cytosol which was modified in vitro with known substitution levels of MAA (FIG. 8B) were used as a standard curve, liver cytosol proteins from ethanol-fed rats were estimated to contain MAA adducts at the level of 75±14 pmoles of acetaldehyde bound per mg protein.

EXAMPLE 4

Monoclonal Anti-MAA Preparation

Syngeneic mouse plasma proteins (MsPP) were modified with MAA (formed by incubating protein with 1 mM MDA and 1 mM AA for three days). Mice were then immunized with the MAA adducted proteins mixed with Freund's complete adjuvant. The mice were boosted with freshly prepared MAA adducted MsPP in Freund's incomplete adjuvant. Two weeks after the last boost, mice were sacrificed and the spleens removed. A suspension of single cells was obtained from the spleens and fused with mouse NS-1 cells using traditional fusion methods (polyethylene glycol). Hybridomas were screened for production of antibody against different proteins unmodified or modified with 1 mM AA, 1 mM MDA, or MAA. Well containing hybrids that produced antibody which recognized only MAA adducts on proteins were selected. These mixed hybrids were then cloned by standard limiting dilution techniques. The isotype of the monoclonal antibody was determined by an antigen capture ELISA and then purified by affinity chromatography using a Staph Protein A column.

EXAMPLE 5

Polyclonal Rabbit Anti-MAA Preparation

Syngeneic rabbit plasma protein (RbPP) modified with MAA was mixed with Freund's complete adjuvant and used to immunize rabbits by subcutaneous injections of the material at three sites along the back. The rabbits were boosted twice with freshly prepared MAA adducted RbPP in Freund's incomplete adjuvant. Two weeks after the last booster injection, rabbits were bled from the marginal ear vein by venapuncture. The serum obtained was tested in an ELISA for activity to proteins which were either unmodified or modified with 1 mM AA, 1 mM MDA or MAA. Antibody was first purified by affinity chromatography using a MAA modified lysine-sepharose 4B followed by further purification on a protein G column. This rabbit preparation was >95% IgG and contained antibody specific only for MAA adducts regardless of the carrier protein.

EXAMPLE 6

Human Studies

Blood from pati nts admitted to the Substance Abus Treatment Program and the Omaha VA Medical Center was obtained in compliance with the guidelines set forth by the Human Review Board. Serum from these patients was tested fro IgM and IgG antibody activity against unmodified proteins or carrier proteins modified with one of the following:

1 mM AA 1 mM MDA

MAA 100 mM AA 5 mM AA with 30 mM sodium cyanoborohydrate 240 mM AA with 100 mM sodium cyanoborohydrate.

No significant differences were found in the quality of IgG antibody activity to any of the adducts when comparisons were made between controls and alcoholic patients. For example, IgG antibody responses were detected in 65% (29/44, geometric mean titer of 1000) of the alcoholic patients compared to 59% of the controls (13/22, geometric mean titer of 100). However, there were differences in the quantity of IgG antibody since the geometric mean titer of IgG antibody was approximately tenfold higher in alcoholic patients compared to control patients.

IgM antibody activity to the MAA adduct showed some differences when comparing groups in that 23% (10/44) of alcoholic patients had IgM antibody to the MAA adduct (mean titer of 1:100) in contrast to no demonstrable activity in control serum.

Serum from these same patients was also screened for circulating immune complexes containing antigens that had been modified with MAA adducts in vivo. This was accomplished by capturing (immobilizing) antigen-antibody complexes using a patented reagent, RhC, coated onto the wells of polystyrene plates. MAA adducts associated with the captured immune complexes were detected by probing the complexes with biotinylated Mab with specificity to the MAA adduct. The results showed that approximately 18% of the alcoholic patients had circulating immune complexes containing MAA adducted proteins as detected by Mab anti-MAA.

In another pilot study, immune complexes were isolated from the plasma of 50 patients. These complexes were solubilized and analyzed by Western blot using the biotinylated Mab anti-MAA as the probe. Bands of approximately 70 kDa were detected in only 4 patients, all of whom were diagnoses with alcoholic liver disease. These bands were not found in any other patient regardless of th ir diagnosis. This data suggest that MAA adducted proteins are involved in immune responsiveness related to alcohol liver disease and are either involved in or result from the condition.

Further support for the conclusion that MAA-protein adducts presents unique and distinct chemical structures can be obtained by consideration of the studies of Ohya. Ohya T. "Formation of a new 1,1,1 adduct in the reaction of malondialdehyde, n-hydroxylamine and alkanal under neutral conditions." Biol Pharm bull 1993; 16: 137–141. In his studies, investigating the reaction of MDA and alkanals with primary amines under neutral conditions, he observed the formation of two major products. These products were identified as a 1:1:1 adduct and a 2:1:1 adduct of MDA, alkanal and primary amine, respectively. If these findings are extrapolated to include the reaction of MDA and acetaldehyde with ε-amino group of lysine (or perhaps α-amino terminus as well) in proteins. The cyclic 2:1 adduct (FIG. 10B) has been shown to be highly fluorescent and, therefore, the formation of this adduct contributes to the fluorescence of MAA adducts observed in applicants' studies. In contrast to the complexity and heterogeneity associated with structural assignments for acetaldehyde-protein adduct and MDA-protein adducts, definitive chemical structures can be proposed for MAA adducts.

Another feature of MAA adduct formation with proteins is the production of immunodominant antigenic determinants. A high titer polygonal antibody was raised in rabbits by immunization of rabbit plasma proteins that had been treated with only 1 mM concentrations of acetaldehyde and MDA. After affinity purification with MAA-lysine, the antibody showed a high specificity for MAA epitopes on proteins and did not react with acetaldehyde-treated, or carrier proteins. It recognized MAA epitopes on a variety of protein carriers which were modified with either high or low concentrations of aldehydes. This specific antibody was then used to develop an immunochemical assay for the detection and quantification of MAA adducts in biological samples.

A sensitive ELISA was developed to determine the extent of MAA modification of liver proteins during the chronic administration of ethanol to rats. The assay had a high specificity for MAA derivatives of proteins, and the extent of MAA modification was the most important factor in determining the efficiency of inhibition of antibody binding in this system. These factors indicate the applicability of this assay for not only the detection of MAA adducts but their quantification as well. When liver cytosol proteins, which were previously modified in vitro by low levels of MAA conjugation, were tested the assay proved to be effective in quantifying the extent of MAA modification in the pmolar range (FIG. 8). The quantification of MAA was based on pmoles of acetaldehyde bound because it appears, based on the proposed structures of MAA adducts (FIG. 10), that there is one mole of acetaldehyde per mole of MAA derivative.

MAA-modified proteins in liver cytosol from ethanol-fed rats were readily detected by the competitive ELISA; whereas, little or no immunoreactability to MAA adducts was observed in cytosol proteins from the pair-fed controls (FIG. 9). Quantification of the inhibition curves of the competitive ELISA indicated an estimate of MAA modification to be about 75 pmoles of MAA per mg of liver cytosol proteins of the ethanol-fed animals. Thus, significant formation of MAA adducts occurs on liver cytosol proteins during chronic ethanol administration to rats.

Numerous studies in the literature have applied immunochemical techniques to indicate the presence of a variety of protein adducts in the livers of ethanol-treated animals. These would include acetaldehyde adducts, MDA adducts, and more recently hydroxyethyl radical-derived adducts. However, structural information and epitope characterization of these adducts are lacking, and quantitative data have not been reported. In contrast, the applicants have provided quantitative estimates for MAA adduct formation and proposed structures of the MAA adducts. Furthermore, the results indicate that MDA and acetaldehyde react together in a synergistic manner which demonstrates that MAA adduct formation would be favored over adducts formed with acetaldehyde of MDA alone and that MAA adducts may represent a major species of adducts formed in the liver during ethanol metabolism in vivo. Since both the covalent binding of acetaldehyde to proteins and increased lipid peroxidation have been proposed as possible mediators of ethanol-induced liver injury, MAA protein-adduct formation represents an event dependent on both mechanisms, suggesting a common or unifying process (i.e. MAA adduct formation) by which both mechanisms can contribute to alcohol hepatotoxicity.

EXAMPLE 7

Recently it was shown that the concomitant incubation of protein with MDA and AA synergistically increased the amount of adduction and resulted in the production of a new epitope (MAA). This epitope was shown to be immunogenic without the use of adjuvant and can be produced under conditions that begin to approach physiological levels (1 mM) of AA and MDA. The purpose of this study was to determine how modification of a soluble carrier protein with the MAA adduct alters the humoral immune response. Balc/c mice were immunized weekly by i.p. injection with 100 $\mu$g of either bovine serum albumin unmodified (BSA) or modified with MAA (BSA-MAA). Titration of antiserum was performed by ELISA on wells coated with either BSA, BSA-MAA, mouse albumin (MSA) and MSA-MAA. In further studies to examine the level of protein necessary to induce this immune response, 12 groups of mice (5/group) were immunized with one of the six doses of BSA or BSA-MAA: 100 $\mu$g, 50 $\mu$g, 25 $\mu$g, 10 $\mu$g, 5 $\mu$g, and 1 $\mu$g. results show that in mice immunized with 100 $\mu$g of BSA-MAA, serum antibody titers to both BSA and BSA-MAA reached maximal levels at 3 weeks (>1:3200). Further testing on MSA and MSA-MAA demonstrated a significant antibody titer to the MAA adduct, but no response to the autologous protein. In mice immunized with lower concentrations of BSA-MAA, antibody titers decreased in a dose dependent manner to both BSA and BSA-MAA (>1:3200 at 100 μg to 1:2000 at 25 μg). Surprisingly, antiserum from mice immunized with 25 μg of BSA-MAA recognized epitopes on the BSA polypeptide chain and not the MAA adduct itself. BSA without MAA adduction elicited a weak antibody response to only BSA and only at high doses (>50 μg). Therefore, these data indicate that the adduction of protein with MAA enhances their immunogenicity and further suggest that MAA adduction stimulates the targeting, processing, and/or presentation of the carrier protein to the humoral immune system.

EXAMPLE 8

Proteins (at 2 mg/ml) were incubated with 1 mM AA and/or 1 mM MDA for 3 days at 37° C. Rabbits were immunized subcutaneously with MAA-modified rabbit plasma proteins (RbPP) in Freunds' adjuvant. Mice were immunized intraperitoneally with MAA-modified mouse plasma proteins (MsPP) in Freunds' adjuvant. Polyclonal rabbit serum was affinity-purified to the MAA-adduct using lysine-sepharose 4B beads modified with 1 mM MDA and 1 mM AA for 16 hours at 37° C. Antibody was purified using standard affinity chromatography methods. Spleen cells from mice immunized with MsPP-MAA were fused with myelomas using established methods to produce hybridomas secreting MAA-specific monoclonal antibodies that were purified using protein G. To determine specificity, the antisera and purified antibodies were titered against RbPP, MsPP and BSA modified with nothing, AA, MDA or MAA. Antisera from rabbits and mice showed antibody titers of 1:12,800 and 1:6400, respectively to the MAA adduct and not to the syngeneic carrier protein. Both antisera showed minor reactivity to AA- and MDA-modified proteins (1:200 or less). Affinity purification of rabbit antibody and the production of mouse monoclonal antibodies resulted in high-titered antibody specific for only the MAA-adduct and capable of detecting MAA on a variety of different proteins. Recently, using a competitive inhibition ELISA, the presence of MAA-adducted proteins in the livers of rats chronically-fed alcohol has shown. Therefore, the use of these antibodies may prove useful in determining the physiological relevance of MAA-associated proteins in the development and/or progression of ALD.

EXAMPLE 9

An immunological assay, using an affinity-purified polyclonal antibody specific for MAA adducts, was employed to detect the presence of these adducts in livers of ethanol-fed rats. Since MAA adducts are likely composed of more than one distinct product, applicants proposed that 4-methyl-1, 4-dihydropyridine-3,5-dicarbaldehyde (MDDC), derivatized to an ε-amino group of lysine, represents a structure for one of the major MAA-protein adducts. The purpose of this study was to characterize the antigen binding properties of the MAA specific antibody and determine whether MDDC epitopes are a major determinant of antibody recognition. A competitive ELISA, utilizing bovine serum albumin-MAA as the solid phase antigen, was used to test the binding specificity of the antibody. The most effective inhibitor of antibody binding in this assay, with a 50% inhibitory concentration of 4 pmoles/well, was 1-hexyl-MDDC, which simulates a MDDC group attached to a lysyl residue of a protein. Analogs of 1-methyl and 1-hydrogen MDDC had increased 50% inhibitory concentrations of 14 and 240 pmoles/well, respectively. Substitutions at the 4-position of MDDC had even greater effects. Replacement of the 4-methyl with a 4-hexyl or 4-cyclohexyl group resulted in 3800- and 20,000-fold increases in the 50% inhibitory concentrations, respectively. Endogenous liver compounds with structures related to 1-hexyl-MDDC, such as NADH and pyridoxal, produced negligible inhibitions of antibody binding. When 8 different MAA-adducted proteins were tested in our competitive ELISA and the resulting inhibitions expressed as a function of th number of lysyl-MDDC residues per protein, the 50% inhibitory concentrations of these various MAA-protein adducts ranged from 1 to 31 pmoles of lysyl-MDDC equivalents/well. Digestions of these proteins with pronase markedly narrowed the range of the observed 50% inhibitory concentrations (6 to 15 pmoles/ well), indicating that protein hydrolysis equalized the accessibility of the antibody to bind the epitope on these various proteins. These results indicate that our MAA-adduct specific antibody predominantly recognizes the 1-lysyl MDDC residue on proteins and can be effectively used to detect and quantify MAA adducted proteins.

The above description sets forth novel MAA adducts useful for the detection of liver disease and defines the adducts chemically. It further describes polygonal and monoclonal antibodies which are useful for detecting the presence of the novel acetaldehyde/malondialdehyde protein adducts of the present invention. Also, the description provides methods of use for the novel adducts through immunoassays. It is thus submitted that the present invention accomplishes at least all of its stated objectives.

What is claimed is:

1. A method of detecting the presence of alcohol liver disease comprising:

collecting a sample of serum, plasma or urine; and assaying for the presence of a hybrid malondialdehyde-acetaldehyde (MAA)

protein adduct, said adduct having the following formula:

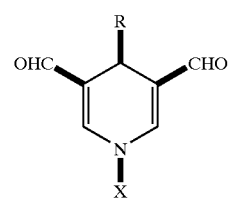

wherein X is a peptide or protein containing an active lysine residue; and R is selected from the group consisting of a lower $C_1$ to $C_6$ alkyl group, benzyl and hydrogen, wherein increased MAA protein adduct, when compared against levels in a person not suffering from alcohol liver disease, is associated with alcohol liver disease.

2. The method of claim 1 wherein said method of detection is by fluorescence detection at 397 nm.

3. The method of claim 1 wherein said detection is by an immunoassay comprising an antibody which recognizes a MAA epitope, said antibody being a monoclonal or polyclonal antibody.

* * * * *